United States Patent [19]

Sunshine et al.

[11] Patent Number: 4,851,444

[45] Date of Patent: Jul. 25, 1989

[54] ONSET-HASTENED/ENHANCED ANALGESIA

[75] Inventors: Abraham Sunshine, New York; Eugene M. Laska, Larchmont, both of N.Y.

[73] Assignee: Analgesic Associates, Larchmont, N.Y.

[21] Appl. No.: 71,914

[22] Filed: Jul. 10, 1987

[51] Int. Cl.$^4$ ............................................. A61K 31/19
[52] U.S. Cl. .................................... 514/570; 514/557; 514/960; 514/962; 514/947
[58] Field of Search .............................. 514/557, 570

[56] References Cited

U.S. PATENT DOCUMENTS 4,555,524  11/1985  Gruber et al. ...................... 514/570
4,690,823   9/1987  Lohner et al. ...................... 514/570

FOREIGN PATENT DOCUMENTS 0267321  5/1988  European Pat. Off. .

OTHER PUBLICATIONS

Biochemical Pharmacology, vol. 35, No. 19 (Oct. 1986), pp. 3403-3405, Pergamon Journals Ltd., K. Williams et al., "The Steroselective Uptake of Ibuprofen Enantiomers into Adipose Tissue".
Current Medical Research and Opinion, vol. 3, No. 8 (1975), p. 552, S. S. Adams et al., "The Optical Isomers of Ibuprofen".
J. Pharm. Pharmacol., vol. 28 (1976), pp. 256-257, S. S. Adams et al., "Pharmacological Difference Between the Optical Isomers of Ibuprofen: Evidence for Metabolic Inversion of the (−)—Isomer".
Journal of Pharmaceutical Sciences, vol. 56 (1967), p. 1686, S. S. Adams et al., "Some Biological Properties of 2—(4—Isobutylphenyl)—Propionic Acid".
Biochemical and Biophysical Research Communications, bol. 61, No. 3 (1974), pp. 833-837, W. J. Wechter et al., "Enzymatic Inversion at Saturated Carbon: Nature and Mechanism of the Inversion of R(−) p—iso—Butyl Hydratropic Acid".
J. Pharm. Pharmacol., vol. 35 (1983), pp. 693-704, Andrew J. Hutt et al., "The Metabolic Chiral Inversion of 2—Arylpropionic Acids—A Noval Route with Pharmacological Consequences".
Clinical Pharmacokinetics, vol. 9 (1984), pp. 371-373, Andrew J. Hutt et al., "The Importance of Stereo—Chemistry in the Clinical Pharmacokinetics of the 2-A-rylproprionic Acid Non–Steroidal Anti–Inflammatory Drugs".
The Journal of Pharmacology and Experimental Therapeutics, vol. 232, No. 3 (1985), pp. 636-643, J. W. Cox et al., "Ibuprofen Stereoisomer Hepatic Clearance and Distribution in Normal and Fatty in Situ Perfused Rat Liver".
Clinical Pharmacology & Therapeutics, vol. 41, No. 2 (Feb. 1987), p. 200.
Clinical Pharmacology & Therapeutics, vol. 40, No. 1 (1986), pp 1-7, Eugene M. Laska et al., "The Correlation Between Blood Levels of Ibuprofen and Clinical Analgesic Response".
Chemical Abstracts, vol. 106 (1987), Abstract No. 66922r (Daicel Chemical Industries, Ltd.).
Physicians' Desk Reference, 40th Edition (1986), pp. 1854-1855, Edward R. Barnhart.
Xenobiotica, vol. 3, No. 9 (1973), pp. 589-598, R. F. N. Mills et al., "The Metabolism of Ibuprofen".
Journal of Pharmaceutical Sciences, vol. 64, No. 5 (1975), pp. 798-801, Garrett J. Vangiessen et al., "GLC Determination of Ibuprofen [dl-2-(p-Isobutylphenyl)-Propionic Acid] Enantiomers in Biological Specimens".
Journal of Pharmaceutical Science, vol. 65, No. 2 (Feb. 1976), pp. 269-273, D. G. Kaiser et al., "Isomeric Inversion of Ibuprofen (R)-Enantiomer in Humans".
Anti-Inflammatory and Anti-Rheumatic Drugs, Eds. Rainsford and Path, CRC Press Inc., Boca Raton, Fla. (1985), p. 172, Anthony C. Allison et al., "Naproxen".
Angew. Chem. Internat. Edit., vol. 11, No. 6 (1972), pp. 460-472, T. Y. Shen, "Perspectives in Nonsteroidal Anti-Inflammatory Agents".
Nonsteroidal Anti-Inflammatory Agents, Chapter 62 in Burger's Medical Chemistry, 4th Edition, Part III, Wiley Interscience, New York (1981), pp. 1205-1271, T. Y. Shen.
Br. J. Clin. Pharmac., vol. 19 (1985), pp. 669-674, E. J. D. Lee et al., "Stereoselective Disposition of Ibuprofen Enantiomers in Man".
The Journal of Pharmacology and Experimental Therapeutics, vol. 148, No. 3 (1965), pp. 373-379, Charles A. Winder et al., "Nociceptive Thresholds as Affected by Parenteral Administration of Irritants and of Various Antinociceptive Drugs".
Proceedings of the Society for Experimental Biology and Medicine, vol. 118, (1965), pp. 763-766. H. Blumberg et al., "Use of Writhing Test for Evaluating Analgesic Activity of Narcotic Antagonists".
Journal of Pharmaceutical Sciences, vol. 73, No. 11 (Nov. 1984), pp. 1542-1544, E. J. D. Lee et al., American Pharmaceutical Association, "Liquid Chromatographic Determination and Plasma Concentration Profile of Optical Isomers of Ibuprofen in Humans".
Remington's Pharmaceutical Sciences, 15th Edition (1975), Mack Publishing Company, Easton, Pennsylvania 18042, Chapter 59, p. 1054, John E. Hoover.
Caldwell et al., "The Metabolic Chiral Inversion and Dispositional Enantioselectivity of the 2-Arylpropionic Acids and Their Biological Consequences", vol. 37, No. 1, pp. 105-114 (1988).

Primary Examiner—Jacqueline V. Howard
Attorney, Agent, or Firm—Burns, Doane, Swecker & Mathis; 10

[57] ABSTRACT

Onset-hastened and enhanced analgesic response is elicited in a mammalian organism in need of such treatment, i.e., a mammal suffering pain, by administering thereto a unit dosage onset-hastening/enhancing analgesically effective amount of the S(+) ibuprofen enantiomer, said enantiomer being substantially free of its R(−) ibuprofen antipode.

39 Claims, No Drawings

ONSET-HASTENED/ENHANCED ANALGESIA

BACKGROUND OF THE INVENTION

1. Field of the Invention:

The present invention relates to the use of S(+) ibuprofen to elicit an onset-hastened and enhanced analgesic response in mammalian organisms in need of such treatment, and to certain pharmaceutical compositions comprising unit dosage effective amounts of S(+) ibuprofen.

2. Description of the Prior Art:

Ibuprofen, or (±) 2-(p-isobutylphenyl)propionic acid, has the structural formula

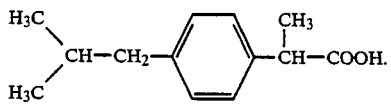

The compound is well-known as a nonsteroidal antiinflammatory drug having analgesic and antipyretic activity. Ibuprofen is currently marketed by prescription in the United States generically, as well as under tradenames such as Motrin ®, which is available in 400, 600 and 800 mg tablets for oral administration. Ibuprofen has recently also become available in this country in non-prescription strength (200 mg) under a variety of tradenames, including Advil ® and Nuprin ®, as well as in generic form. For the treatment of mild to moderate pain, 400 mg every 4 to 6 hours, not to exceed 3200 mg daily, is generally recommended for Motrin ®. The lower dose over-the-counter products are generally recommended for minor aches and pains, to be used orally at the 200 to 400 mg level, every 4 to 6 hours, not to exceed 1200 mg daily unless directed by a physician. See also *Physician's Desk Reference,* 40th edition, 1986, publisher Edward R. Barnhart, Medical Economics Company, Inc., Oradell, N.J. 07649, pp. 1854–1855 and 1897.

As is apparent from its chemical nomenclature, ibuprofen is a racemic mixture. It is only the racemic mixture which has in fact ever been marketed. There have, however, been some studies of the individual S(+) and R(−) isomers reported in the literature. These generally reflect that the R(−) isomer is rapidly converted to the S(+) enantiomer, which is the active form of ibuprofen.

Adams et al, *Curr. Med. Res. Opin.,* 3, 552 (1975) and *J Pharm. Pharmacol.,* 28, 256–257 (1976), reported that in vivo anti-inflammatory and analgesic tests in guinea pigs, rats and mice comparing the dextro (+), levo (−) and racemic mixture forms of ibuprofen showed the three forms to be very similar in potency. (The in vivo tests were conducted in an acetylcholine-induced writhing test in the mouse, in a pain threshold technique test using the yeast-inflamed paw of the rat and using ultraviolet erythema in the guinea pig.) In vitro, however, it was found that nearly all of the activity resided in the dextrorotatory form. The authors concluded that the in vitro results suggested that the dextro (+) form was the active one, but that in vivo the levo form was converted to the dextro form so that there was little difference in pharmacological activity. This was also seen to be an explanation for earlier observations [Adams et al, *J. Pharm. Sci.,* 56, 1686 (1967) and Mills et al, *Xenobiotica,* 3, 589–598 (1973)] that ibuprofen's urinary metabolites in man were found to be dextrorotatory. Thus, it has been recognized for over a decade that the S(+) isomer is the active form.

Wechter et al, *Biochem. Biophys. Res. Commun.,* 61, 833–837 (1974) reported the results of tests in healthy human subjects designed to determine the stereochemistry involved in ibuprofen's metabolism and the relative stereochemical relationships between ibuprofen's optical isomers and its metabolic products. They found there was a facile epimerization of ibuprofen's R(−) isomer to the S(+) isomer and concluded that this accounted for the essential bioequivalence of the R(−) and S(+) isomers.

Related observations were reported by Vangiessen et al, *J. Pharm. Sci.,* Vol 64, No. 5, 798–801 (May 1975), who found that after oral administration of the racemic mixture to human volunteers, the predominant enantiomer in the peripheral circulation and excreted in the urine was of the d-configuration. Vangiessen et al estimated that the plasma drug disappearance half-lives for the d- and l-isomer were 3.34 and 2.01 hours, respectively. The concentration ratio of d to l increased progressively with time from 1.17 at one hour to 2.65 at eight hours; however, these estimates are compromised by the small sample size (n=3), the fact that normal subjects were used, and the extremely large standard deviations from the mean at the earliest (one-hour) post-dosing time point. Interpretation of the results of this study is further compromised because S(+) was not administered alone so that no comparisons with the racemate are possible.

Subsequently, Kaiser et al., *J. Pharm. Sci.,* Vol. 65, No. 2, 269–273 (February 1976) reported on characterization of enantiomeric compositions of ibuprofen's major urinary metabolites after oral administration of the racemic mixture and the individual S(+) and R(−) isomers to healthy human subjects. It was found that only the R(−) enantiomer of the intact drug was inverted to its optical antipode, S(+).

Hutt et al, *J. Pharm. Pharmacol.,* 35, 693–704 (1983), reviewed the earlier work on the metabolic chiral inversion of 2-arylpropionic acids, including ibuprofen, which they indicate was the first substituted 2-arylpropionic acid conclusively shown to undergo the inversion as well as the most studied member of the group. The authors again noted that Adams et al (1976) found no significant difference in in vivo activity among the R(−) and S(+) isomers and the racemic mixture in three different animal models, but very large differences in vitro between the R(−) and S(+) isomers, ascribing this discrepancy to the virtually quantitative conversion of the R(−) to the active S(+) isomer in vivo. Hutt et al indicated similar properties for fenoprofen. The enantiomers of fenoprofen were reported to be of equal potency in animal test systems.

In the same paper, Hutt et al reported that, in contrast, for several other 2-arylpropionic acids, the inactive R(−) isomer was not converted in vivo to the active S(+) isomer as readily as ibuprofen and fenoprofnn, although the conversion seemed to occur to some extent over time. Naproxen, they noted, has been the only compound marketed as the S(+) enantiomer to date. And in the case of indoprofen, the R(−) enantiomer was found to be about 20 times less pharmacologically active in rats and mice in vivo than the S(+) isomer. Hutt et al concluded:

It is likely that benefits will be obtained from the use of the S(+)-enantiomer of 2-arylpropionates as drugs as opposed to the racemates. This is only found at present in the case of naproxen. In cases of rapid inversion, the inactive R(—) isomer serves merely as a prodrug for the active S(+)—antipode. Where inversion is slow, the R(—) enantiomer is an unnecessary impurity in the active S(+) form. Use of the S(+)-enantiomer would permit reduction of the dose given, remove variability in rate and extent of inversion as a source of variability in therapeutic response and would reduce any toxicity arising from non-stereospecific mechanisms.

Thus, in cases of rapid inversion, such as ibuprofen and fenoprofen, where substantially equivalent in vivo responses have been reported for the individual enantiomers and the racemic drug, Hutt et al suggested that no benefits would be obtained from the use of the S(+) isomer because the inactive R(—) isomer merely acts as a prodrug for the active S(+) form. Contrariwise, in cases where chiral inversion is slow, e.g. naproxen and indoprofen, the use of the S(+) enantiomer is desirable for several reasons enumerated by Hutt et al. Indeed, naproxen has been reported to be marketed as the d-isomer for one of the reasons given by Hutt et al, i.e. to reduce side effects (Allison et al, "Naproxen," Chapter 9 in *Anti-inflammatory and Anti-Rheumatic Drugs*, eds. Rainsford and Path, CRC Press Inc., Boca Raton, Fla., 1985, p. 172).

Another general report on earlier work has been provided by Hutt et al in *Clinical Pharmacokinetics*, 9, 371-373 (1984). In this article on the importance of stereochemical considerations in the clinical pharmacokinetics of 2-arylpropionic acids, the authors tabulated relative potencies of the enantiomers of a number of 2-arylpropionic acids in vivo and in vitro. The in vitro results showed the S or (+) isomer in each case to be the active species. In vivo, however, the results were not consistent across the entire class. Thus, the results for naproxen and indoprofen demonstrate the S or (+) isomer to be much more active in vivo, indicating a relatively slow inversion of the inactive R or (—) isomer to the active S or (+) isomer; the results for fenoprofen and ibuprofen, on the other hand, demonstrate the inactive R or (—) and the active S or (+) isomers to be approximately equally effective in vivo, indicating a rapid inversion of R or (—) isomer to S or (+) isomer.

The medicinal chemistry of 2-arylpropionic acids and other NSAIDs (non-steroidal anti-inflammatory drugs) has been reviewed by Shen in *Angewandte Chemie International Edition*, Vol. 11, No. 6, 460-472 (1972) and in "Nonsteroidal AntiInflammatory Agents," Chapter 62 in Burger's Medicinal Chemistry, 4th edition, part III, Wiley Interscience, New York (1981), pp. 1205-1271. In the latter publication, Shen notes that ibuprofen is used as a racemic mixture because the two optical isomers are equally potent in the UV erythema assay, a commonly used anti-inflammatory model.

Lee et al, *Br. J. Clin. Pharmac.* 19, 669-674 (1985), administered racemic ibuprofen and each of the enantiomers separately to four healthy human males, then studied stereoselective disposition. They estimated that about 63% of the dose of R(—) was inverted to the S(+) enantiomer over a 14 hour period. Lee et al noted that the kinetics of the S(+) and R(—) enantiomers were changed when the respective optical antipode was concurrently administered. The authors speculated that this alteration reflected an interaction between the R(—) and S(+) forms at the binding sites for plasma protein. An ibuprofen plasma level time profile for a single subject is shown graphically in the paper and might suggest that there was minimal conversion in the early hours of the study, but the authors did not appear to attach any significance to this. Lee et al indicated that the half-life of S(+) after administering the racemate was 2.5 hours, whereas the half-life of S(+) after administering S(+) was 1.7 hours. The authors recognized the limitations of their work, for reasons including the small number of subjects studied, and an assumption that the clearance of S(+) is unchanged between administrations of R(—) and S(+). They also cautioned that it is quite likely that the fraction of R(—) that is inverted to S(+) varies from individual to individual.

Cox et al, *J. Pharmacol. Exp. Ther.*, Vol. 232, No. 3, 636-643 (1985), carried out liver perfusion experiments to study the role of the liver in the clearance of the stereoisomers of ibuprofen in normal and disease states. Experiments were conducted with normal and fatty rat liver. Results showed that when liver is fatty, clearance of the R(—) isomer is affected and preferential S(+) hepatic distribution is eliminated. However, the effects were predicted to have only minimal impact on total ibuprofen plasma levels following racemic ibuprofen dosing.

Cox et al, abstract in *Amer. Soc. Clin. Pharmacol. Ther.*, February 1987, 200 (abstract PIIL-7) described a three way crossover study in which single doses of ibuprofen solution were given orally to twelve healthy human males. The doses given were 800 mg of racemic ibuprofen, 400 mg of R(—) ibuprofen and 400 mg of S(+) ibuprofen. Based on area-under-the-curve measures, significant chiral inversion was observed for R(—) but not for S(+). Elimination of S(+) was inhibited as plasma concentration of R:S increased. The extent of R(—) inversion, based on urinary data, was the same for the racemate and the R(—) isomer, with a mean of 0.66. Again, the authors gave no information as to what occurred in the first two hours. The statement on reduced clearance of S(+) in the racemate is consistent with the finding of increased length of S(+) half-life after administering the racemate found by Lee et al.

Laska et al, *Clin. Pharmacol. Ther.*, Vol. 40, No. 1, 1-7 (July 1986), reported that administration of racemic ibuprofen to patients with moderate to severe pain subsequent to third molar extraction gave correlations between pain intensity ratings and serum levels of ibuprofen. Correlations were found between contemporaneous serum levels and measures of pain intensity improvement, supporting the proposition that increased ibuprofen serum levels lead to increased analgesia, particularly in the first few hours after dosing. However, the authors did not correlate analgesia with either isomer of ibuprofen; the possibility of critical differences between free and bound ibuprofen and between the S(+) and R(—) isomers was not addressed.

In summary, the current state of the art recognizes that, in mammals, the S(+) form is the active enantiomer of ibuprofen. The art further recognizes that there is a significant, relatively rapid conversion in vivo of R(—) to S(+), with little if any conversion of S(+) to R(—). Furthermore, in the only animal experiments on efficacy reported in the literature, it was noted that there were no significant differences in potency between the racemate and the enantiomers. This is attributed to the rapidity of the chiral inversion. This would suggest there would be no benefit to be derived from the use of S(+) ibuprofen for analgesia. Indeed, use of S(+) alone would appear to reduce the half-life of the active drug. The prior art, moreover, is conspicuously silent in respect to any onset-hastened/enhanced alleviation of mammalian pain utilizing whatever form of the ibuprofen drug species.

SUMMARY OF THE INVENTION

Surprisingly, the present inventors now find that S(+) ibuprofen can be advantageously administered to mammals suffering from pain, especially humans, to not only elicit a more potent analgesic response but also to evoke such response more rapidly than possible by administration of the same dose of ibuprofen in its racemic form.

This is particularly surprising in light of the art's failures to attribute any significative difference in activity in vivo for S(+) ibuprofen versus the racemic mixture, a failure which the present inventors brand as resulting from the lack of telling observations of the pain level or amount of relief at meaningful time points sufficiently soon after dosing in an appropriate analgesic model.

In one aspect, the present invention thus provides a method of hastening the onset of analgesia in a mammal, said method comprising administering to a mammal in need of such treatment an effective onset-hastening analgesic amount of S(+) ibuprofen substantially free of R(−) ibuprofen.

In another aspect, the present invention provides a method of eliciting an enhanced analgesic response in a mammal, particularly shortly after dosing, said method comprising administering to a mammal in need of such treatment an effective analgesia enhancing amount of S(+) ibuprofen substantially free of R(−) ibuprofen.

In yet another aspect, the present invention provides a pharmaceutical composition of matter for use in eliciting an onset hastened and enhanced analgesic response in mammals, especially humans, said composition comprising an effective analgesic unit dosage amount of S(+) ibuprofen substantially free of R(−) ibuprofen. Typically, S(+) ibuprofen is associated with a nontoxic pharmaceutically acceptable inert carrier or diluent therefor.

DETAILED DESCRIPTION OF THE PREFERRED EMBODIMENTS OF THE INVENTION

The term "ibuprofen" or "racemic ibuprofen" as used herein is intended to encompass not only (±) 2-(p-isobutylphenyl)propionic acid itself but also any pharmaceutically acceptable salt thereof, e.g. ibuprofen aluminum.

The term "S(+) ibuprofen" as used herein is intended to encompass not only the dextrorotatory or S(+) isomer of 2-(p-isobutylphenyl)propionic acid but also any pharmaceutically acceptable, analgesically effective salt thereof. The expression "substantially free of R(−) ibuprofen" as used in conjunction with the term "S(+) ibuprofen" means that the S(+) ibuprofen is sufficiently free of R(−) ibuprofen [which is the levorotatory form or R(−) isomer of 2-(p-isobutylphenyl)propionic acid or salt thereof] to exert the desired onset-hastened and enhanced analgesic effect. Practically speaking, this means that the active ingredient should contain at least 90% by weight S(+) ibuprofen and 10% or less by weight R(−) ibuprofen. Preferably, the weight ratio of S(+) ibuprofen to R(−) ibuprofen is greater than 20:1, more preferably greater than 97:3. Most preferably the S(+) ibuprofen is 99 or more % by weight free of R(−) ibuprofen, i.e., the weight ratio of S to R is approximately equal to or greater than 99:1.

Where specific amounts of S(+) ibuprofen are set forth below, it should be understood that, unless otherwise specified, the amounts are given in mg of the acid, not of a salt. Moreover, unless otherwise specified, for simplicity's sake the amounts given represent total ibuprofen content, most of which is in the S(+) form. For example, "400 mg S(+) ibuprofen" means 400 mg total ibuprofen at least 90% of which is in the S(+) form, preferably at least 95%, more preferably at least 97% and most preferably 99% or more.

S(+) ibuprofen, in accord with the present invention, produces the following unexpected results:

(1) the analgesic effect of ibuprofen on the mammal is brought on more quickly than by use of the same dose of racemic ibuprofen; and (2) a greater analgesic response is elicited in the early hours than is elicited by the same dose of racemic ibuprofen.

These unexpected results can be achieved in the treatment of pain responsive to an NSAID (non-steroidal antiinflammatory drug) and specifically pain associated with inflammation. This includes postpartum and postoperative pain, dental pain, headache pain, dysmenorrhea, pain of musculoskeletal origin and pain and discomfort associated with respiratory infections such as colds and flu.

For patients suffering from such pain, who require treatment at a particular dose of racemic ibuprofen, the time from administration of medication to the onset of effective relief is clearly of paramount importance. The present inventors' discovery that S(+) ibuprofen, when used in place of racemic ibuprofen at the same dose, substantially shortens the onset time (i.e., substantially hastens the onset) of analgesia is therefore very significant. It is likewise quite unexpected. Moreover, in patients suffering from inflammatory or degenerative joint disease, e.g. rheumatoid arthritis, osteoarthritis, gout or acute musculo-skeletal disease, the substantial shortening of analgesic onset is extremely important; pain is an important component of these disease states and more rapid relief from pain is of substantial psychological benefit. The S(+) ibuprofen will, of course, over time provide relief from other aspects of inflammatory disease as well, including, e.g. morning stiffness.

In a group responsive to a given dose of the racemate, it is believed that onset time for analgesia can be reached, on the average, about one-third sooner when S(+) ibuprofen is used rather than when racemic ibuprofen is administered, depending on the dose level and the severity of the pain, but particularly at the low end (100–400 mg) of the analgesic dosage range and for patients with moderate pain.

Insofar as concerns enhanced analgesia, more pronounced analgesia is obtained when S(+) ibuprofen is used at the same dose level as racemic ibuprofen, especially during the first few hours.

The precise amount of S(+) ibuprofen for use in accord with the present invention will vary depending, for example, on the size and kind of the mammal and the condition for which the drug is administered. For use in humans, the analgesically effective amount of S(+) ibuprofen will typically be from about 100 to 600 mg, although greater amounts (e.g. 1000 mg) may be employed if needed for pain relief and if tolerated by the patient. The daily dose in humans preferably will not exceed 3200 mg S(+) ibuprofen, although greater amounts could be employed if tolerated by the patient. Preferred unit dosage compositions for use in the treatment of mild to moderate pain having an inflammatory component contain 50, 100, 200, 400, 600 or 800 mg S(+) ibuprofen.

While the compositions for use in the invention are preferably for oral use, they may also be formulated for and administered by other routes which are known for administering non-narcotic analgesics/nonsteroidal anti-inflammatory drugs, e.g. as suppositories or parenteral solutions, or as topical formulations such as ointments, gels, creams, lotions, solutions, impregnated bandages or other topical delivery devices, and so forth. Also, it should be noted that the preferred human dosage levels indicated above are for use in adults; pediatric compositions would contain proportionately less of the active ingredient.

The compositions for use herein are very conveniently administered to mammals by any route of administration suitable for racemic ibuprofen, e.g. oral, rectal, topical or parenteral. Preferably S(+) ibuprofen is formulated with any suitable nontoxic pharmaceutically acceptable inert carrier material. Such carrier materials are well known to those skilled in the art of pharmaceutical formulations. For those not skilled in the art, reference is made to the text entitled *Remington's Pharmaceutical Sciences*, 17th edition, 1985, ed. Alfonso R. Gennaro, Mack Publishing Company, Easton, Pa. 18042. In a typical preparation for oral administration, e.g. tablet, capsule or caplet, S(+) ibuprofen in an effective analgesic amount and substantially free of R(−) ibuprofen, is combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac and/or sugar. Such compositions should preferably contain at least 0.1% of S(+) ibuprofen; generally, S(+) ibuprofen will be from about 2% to about 60% of the weight of the unit. Typical unit dosage forms for oral administration will contain about 50 to 1000 mg, preferably 100 to 800 mg, most preferably 100 to 600 mg, S(+) ibuprofen, if formulated for immediate release, as is preferred. If the composition is intended for sustained release, much larger amounts of the active ingredient would of course be incorporated into an individual unit; in such case, at least 50, and preferably up to 600 or 800 mg of the total amount of S(+) ibuprofen, should be formulated for immediate release so as to obtain the desired degree of enhanced analgesia and hastened onset.

A typical tablet for oral administration may contain, in addition to the selected amount of S(+) ibuprofen, the following combination of inactive ingredients/carrier materials: acacia, acetylated monoglycerides, beeswax, calcium sulfate, colloidal silicon dioxide, dimethicone, iron oxide, lecithin, pharmaceutical glaze, povidone, sodium benzoate, sodium carboxymethylcellulose, starch, stearic acid, sucrose and titanium dioxide; or carnauba wax, cornstarch, D&C Yellow No. 10, FD&C Yellow No. 6, hydroxypropylmethylcellulose, propylene glycol, silicon dioxide, stearic acid and titanium dioxide.

Moreover, the compositions for use in obtaining enhanced analgesia and hastened onset in accord with the present invention may, in addition to the selected dose of S(+) ibuprofen, also contain other active ingredients and/or enhancing agents. Thus, for example, S(+) ibuprofen may be combined with such ingredients and agents as have been described for combination with racemic ibuprofen, e.g. caffeine or other xanthine derivative, a narcotic analgesic (with or without caffeine), a skeletal muscle relaxant, an antihistamine, decongestant, cough suppressant and/or expectorant. See, for example, Sunshine et al U.S. Pat. No. 4,420,483, issued Dec. 13, 1983; Sunshine et al U.S. Pat. No. 4,464,376, issued Aug. 7, 1984; Sunshine et al U.S. Pat. No. 4,479,956, issued Oct. 30, 1984; Sunshine et al U.S. Pat. No. 4,552,899, issued Nov. 12, 1985; Sunshine et al U.S. Pat. No. 4,558,051, issued Dec. 10, 1985; Sunshine et al U.S. Pat. No. 4,585,783, issued Apr. 29, 1986; and Sunshine et al U.S. Pat. No. 4,619,934, issued Oct. 28, 1986; and Sunshine et al pending U.S. patent application Ser. No. 815,502, filed Jan. 2, 1986.

The enhanced analgesic effect and hastened onset obtained by use of S(+) ibuprofen in comparison with racemic ibuprofen can be evaluated in animal and human studies such as those described below.

Antiphenylquinone Writhing Test

This test is a standard procedure for detecting and comparing analgesic activity and generally correlates well with human efficacy.

Mice are first dosed with the medications studied. The medications used are two dose levels of S(+) ibuprofen and two dose levels of racemic ibuprofen. The mice are then challenged with phenyl-p-benzoquinone given intraperitoneally and observed for the characteristic stretch-writhing syndrome. Lack of writhing constitutes a positive response. The degree of analgesic protection can be calculated on the basis of suppression of writhing relative to control animals run the same day. Time response data are also obtained. Observations are made early enough post-dosing to detect differences in onset. The test is a modification from the methods of Sigmund et al and Blumberg et al (Sigmund, E., Cadmus, R., and Lu, G., *Proc. Soc. Exp. Biol. and Med.* 95, 729–731, 1957; Blumberg, H., et al, *Proc. Soc. Exp. Biol. and Med.* 118, 763–766, 1965).

The Inflamed Rat Paw Test: Pressure Induced Stimuli

The method of Randall-Selitto, modified according to Winter et al, is used to ascertain the escape response threshold resulting from the application of increasing pressure to the yeast inflamed left hind paw. Drug treatment is given. The medications studied are two dose levels of S(+) ibuprofen and two dose levels of racemic ibuprofen. A constantly increasing force is applied to the paw and the "flight reaction" is observed and recorded at several points in time (Randall, L. Q., and Selitto, J. J.: *Arch. Int. Pharmacodyn.*, II, 409-419, 1957; Winter, C. A., and Lars, F.: *J. Pharmacol. Exp. Therap.* 148, 373-379, 1965). Observations are made early enough post-dosing to detect differences in onset.

To establish the efficacy of the compositions of this invention in humans, patients with moderate to severe pain requiring an oral analgesic/anti-inflammatory agent, can be administered S(+) ibuprofen or racemic ibuprofen. Typical pain models include dysmenorrhea, post-operative pain, post-partum pain and dental extraction pain. Either a crossover design or a completely randomized design can be used. To determine analgesic efficacy, an observer interviews the patients as to their level of pain at subsequent periods of time. Patients are asked to subjectively estimate the time at which the medication begins to provide significant relief. Patients may be given a stopwatch to help estimate onset more accurately. Appropriate statistical methods, including survival analysis, can be used to show that the S(+) enantiomer has shorter onset and is more efficacious (Laska, E., Gormely, M., Sunshine, A., Belleville, J. W., Kantor, T., Forrest, W. H., Siegel, C. and Meisner, M., "A Bioassay Computer Program for Analgesic Clinical Trials," *Clin. Pharmacol. Ther.* 8:658, 1967; Cox, D.R., "Regression Models and Life Tables," *Journal Royal Statistical Society*, Series B, Volume 34:187-202, 1972).

S(+) ibuprofen for use in the method and compositions of the present invention can be prepared by a variety of methods, such as by resolution of racemic ibuprofen.

Resolution of racemic ibuprofen has been described in the literature. Kaiser et al, *J. Pharm. Sci.*, Vol. 65, No. 2, 269-273 (February 1976) added S(−) α-methylbenzylamine dropwise, with stirring, to a cooled solution of racemic ibuprofen in ether. The solid S(−) α-methylbenzylamine salt of S(+) ibuprofen thus obtained was removed by filtration, recrystallized first from isopropanol and then from methanol, acidified with 3N aqueous sulfuric acid, extracted with ether and washed with water and saline solution. The ether extract was evaporated to dryness and the resultant white solid was recrystallized from ethanol to give S(+) ibuprofen, m.p. 50°14 52°, $[\alpha]_D + 57°$, with 95% optical purity as determined by GLC analysis as the S(−) α-methylbenzylamide derivative. Cox et al, *J. Pharmacol. Exp. Ther.*, Vol. 232, No. 3, 636-643 (March 1985), using Kaiser et al's method, were able to obtain an S(+) ibuprofen preparation which was 99% S isomer and 1% R isomer (w/w).

Generally speaking, the S(+) isomer can be separated from racemic ibuprofen by preparing a salt of ibuprofen with an alkaloid or similar resolving agent such as cinchonidine, then separating the products by fractional crystallization from a solvent in which the dextrorotatory isomer is least soluble. The d-salt can then be acid cleaved to yield S(+) ibuprofen. Compare, for example, Alvarez U.S. Pat. No. 3,637,767, issued Jan. 25, 1972, which relates to resolution of naproxen and related compounds.

When S(+) ibuprofen is to be employed in the form of a pharmaceutically acceptable, analgesically active salt thereof, such salt may be conveniently prepared by direct salification of S(+) ibuprofen. Compare Armitage et al U.S. Pat. No. 4,501,727, issued Feb. 26, 1985, which describes the N-methyl-D-glucamine salt of flurbiprofen. Such a salt may not only be used in oral or rectal compositions, but, if sufficiently soluble in water, may be useful in the preparation of aqueous solutions of S(+) ibuprofen for parenteral injection.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalence of the following claims.

What is claimed is:

1. The method of eliciting an onset-hastened and enhanced analgesic response in a human mammal suffering from pain and in need of such treatment, comprising administering to such organism a unit dosage onset-hastening/enhancing analgesically effective amount of the S(+) ibuprofen enantiomer, and said enantiomer being substantially free of its R(−) ibuprofen antipode.

2. A method according to claim 1, wherein the weight ratio of S(+) ibuprofen to R(−) ibuprofen is greater than 9:1.

3. A method according to claim 2, wherein the weight ratio of S(+) ibuprofen to R(−) ibuprofen is greater than 20:1.

4. A method according to claim 3, wherein the weight ratio of S(+) ibuprofen to R(−) ibuprofen is greater than 97:3.

5. A method according to claim 4, wherein the weight ratio of S(+) ibuprofen to R(−) ibuprofen is approximately equal to or greater than 99:1.

6. A method according to claim 1, comprising administering to such organism from about 50 to about 1000 mg S(+) ibuprofen.

7. A method according to claim 1, comprising administering to such organism from about 100 to about 800 mg S(+) ibuprofen.

8. A method according to claim 1, comprising administering to such organism from about 100 to about 600 mg S(+) ibuprofen.

9. A method according to claim 2, comprising administering to such organism from about 50 to about 1000 mg S(+) ibuprofen.

10. A method according to claim 2, comprising administering to such organism from about 100 to about 800 mg S(+) ibuprofen.

11. A method according to claim 2, comprising administering to such organism from about 100 to about 600 mg S(+) ibuprofen.

12. A method according to claim 3, comprising administering to such organism from about 50 to about 1000 mg S(+) ibuprofen.

13. A method according to claim 3, comprising administering to such organism from about 100 to about 800 mg S(+) ibuprofen.

14. A method according to claim 3, comprising administering to such organism from about 100 to about 600 mg S(+) ibuprofen.

15. A method according to claim 4, comprising administering to such organism from about 50 to about 1000 mg S(+) ibuprofen.

16. A method according to claim 4, comprising administering to such organism from about 100 to about 800 mg S(+) ibuprofen.

17. A method according to claim 4, comprising administering to such organism from about 100 to about 600 mg S(+) ibuprofen.

18. A method according to claim 5, comprising administering to such organism from about 50 to about 1000 mg S(+) ibuprofen.

19. A method according to claim 5, comprising administering to such organism from about 100 to about 800 mg S(+) ibuprofen.

20. A method according to claim 5, comprising administering to such organism from about 100 to about 600 mg S(+) ibuprofen.

21. A method according to claim 1, wherein such organism is suffering from postoperative pain.

22. A method according to claim 1, wherein such organism is suffering from postpartum pain.

23. A method according to claim 1, wherein such organism is suffering from dental pain.

24. A method according to claim 1, wherein such organism is suffering from dysmenorrhea.

25. A method according to claim 1, wherein such organism is suffering from headache pain.

26. A method according to claim 1, wherein such organism is suffering from musculoskeletal pain.

27. A method according to claim 1, wherein such organism is suffering from pain or discomfort associated with a respiratory infection.

28. A method according to claim 1, wherein such organism is suffering from pain or discomfort associated with a cold or flu.

29. A method according to claim 1, wherein such organism is suffering from pain associated with inflammatory or degenerative joint disease.

30. A method according to claim 1, wherein such organism is suffering from pain associated with rheumatoid arthritis.

31. A method according to claim 1, wherein such organism is suffering from pain associated with osteoarthritis.

32. A method according to claim 1, wherein such organism is suffering from pain associated with gout.

33. A method according to claim 1, wherein such organism is suffering from pain associated with morning stiffness.

34. A method according to claim 1, wherein the S(+) ibuprofen is orally administered to such organism.

35. A method according to claim 1, wherein the S(+) ibuprofen is rectally administered to such organism.

36. A method according to claim 1, wherein the S(+) enantiomer is topically administered to such organism.

37. A pharmaceutical composition of matter adapted to elicit an onset-hastened and enhanced analgesic response in a mammalian organism in need of such treatment, said composition comprising a solid-state unit dosage onset-hastening/enhancing analgesically effective amount of the S(+) ibuprofen enantiomer, said enantiomer being substantially free of its R(−) antipode, and a nontoxic pharmaceutically acceptable carrier or diluent therefor.

38. The pharmaceutical composition of matter according to claim 37, adapted for oral administration.

39. The pharmaceutical composition of matter according to claim 38, formulated as a tablet, caplet, pill or capsule.

* * * * *